(12) United States Patent
Kuwano et al.

(10) Patent No.: US 8,865,119 B2
(45) Date of Patent: Oct. 21, 2014

(54) METHOD FOR PROCESSING ACIDIC SOLUTION THAT CONTAINS IODIDE IONS AND IRON IONS

(75) Inventors: Kenichi Kuwano, Hitachi (JP); Atsuko Abe, Hitachi (JP); Manabu Manabe, Hitachi (JP); Akira Miura, Hitachi (JP)

(73) Assignee: JX Nippon Mining & Metals Corporation, Tokyo (JP)

( * ) Notice: Subject to any disclaimer, the term of this patent is extended or adjusted under 35 U.S.C. 154(b) by 13 days.

(21) Appl. No.: 13/698,358

(22) PCT Filed: May 19, 2011

(86) PCT No.: PCT/JP2011/061547
§ 371 (c)(1),
(2), (4) Date: Nov. 16, 2012

(87) PCT Pub. No.: WO2011/145688
PCT Pub. Date: Nov. 24, 2011

(65) Prior Publication Data
US 2013/0058846 A1    Mar. 7, 2013

(30) Foreign Application Priority Data
May 19, 2010    (JP) ................. 2010-128300

(51) Int. Cl.
*B01D 11/00* (2006.01)
*C22B 3/18* (2006.01)
*C12P 3/00* (2006.01)
*C02F 3/34* (2006.01)
*C01B 7/14* (2006.01)
*C22B 15/00* (2006.01)
*C02F 101/20* (2006.01)
*C02F 101/12* (2006.01)
*C02F 1/28* (2006.01)

(52) U.S. Cl.
CPC ... *C12P 3/00* (2013.01); *C22B 3/18* (2013.01); *C02F 2101/203* (2013.01); *C02F 2101/12* (2013.01); *C02F 3/346* (2013.01); *C02F 1/283* (2013.01); *C01B 7/14* (2013.01); *C22B 15/0063* (2013.01)
USPC .............. 423/659; 423/27; 423/41

(58) Field of Classification Search
None
See application file for complete search history.

(56) References Cited

U.S. PATENT DOCUMENTS

| | | | |
|---|---|---|---|
| 4,483,754 A | 11/1984 | Shiroki | |
| 5,914,441 A * | 6/1999 | Hunter et al. | 75/712 |
| 6,168,766 B1 | 1/2001 | Imai et al. | |
| 8,257,671 B2 * | 9/2012 | Kuwano et al. | 423/24 |
| 8,287,623 B2 * | 10/2012 | Manabe | 75/742 |
| 2009/0241734 A1 | 10/2009 | Imagawa et al. | |
| 2010/0018349 A1 | 1/2010 | Manabe | |
| 2011/0041654 A1 | 2/2011 | Manabe | |

FOREIGN PATENT DOCUMENTS

| | | |
|---|---|---|
| JO | 10-265864 A | 10/1998 |
| JP | 62-34681 B2 | 7/1987 |
| JP | 4-16554 B2 | 3/1992 |
| JP | 7-91666 B2 | 10/1995 |
| JP | 9-253523 A | 9/1997 |
| JP | 10-273742 A | 10/1998 |
| JP | 2003-73752 A | 3/2003 |
| JP | 2009-228094 A | 10/2009 |
| JP | 2009-228109 A | 10/2009 |
| JP | 2010-24511 A | 2/2010 |
| JP | 2011-42858 A | 3/2011 |

OTHER PUBLICATIONS

International Search Report issued in PCT/JP2011/061547, mailed on Jul. 5, 2011.
International Preliminary Report on Patentability, and English translation of the Written Opinion of the International Searching Authority, (Forms PCT/IB/338, PCT/IB/373, and PCT/ISA/237) dated Dec. 20, 2012 for International Application No. PCT/JP2011/061547.

* cited by examiner

*Primary Examiner* — Steven Bos
(74) *Attorney, Agent, or Firm* — Birch, Stewart, Kolasch & Birch, LLP

(57) ABSTRACT

Provided is a method for separating and recovering iodine ingredients from acid solution containing iodide ions and iron (II) ions and for efficiently producing iron (III) ions. Said method is for treating acid solution containing the iodide ions and the iron (II) ions. Said method comprises a step of oxidizing the iron (II) ions in said solution into iron (III) ions with iron-oxidizing microorganisms, the step being performed in the presence of activated carbon.

17 Claims, 3 Drawing Sheets

METHOD FOR PROCESSING ACIDIC SOLUTION THAT CONTAINS IODIDE IONS AND IRON IONS

FIELD OF INVENTION

The present invention relates to a method for leaching from a copper sulfide ore. Particularly, the present invention relates to a method for effectively regenerating requisite iron (III) ions using iron-oxidizing microorganisms in leaching of the copper sulfide ore with iodide ions.

BACKGROUND OF THE INVENTION

As for a general method of hydrometallurgy for leaching from a copper sulfide ore, the following methods are known:
leaching according to batch-wise stirring reaction using a sulfuric acid or a hydrochloric acid;
leaching where a heap is formed, a sulfuric acid or a hydrochloric acid is provided from its top and gravity fall droplet is recovered (heap leaching); and
leaching effectively copper to recover using bacteria such as iron-oxidizing microorganisms (bioleaching).

With regards to hydrometallurgy for a copper sulfide ore, bioleaching is practicalized for secondary copper sulfide ores such as chalcocite and covellite. However, primary copper sulfide ores such as chalcopyrite is extremely poorly solubilized into an inorganic acid. Therefore, bioleaching from them under normal temperature, its leaching rate is quite slow.

With regards to the problem of leaching rate, Japanese Patent Appln Publication No. 2011-42858 (hereafter referred to as Patent Document 1) reports that leaching from a copper sulfide ore which primarily contains such as chalcopyrite and enargite is enhanced at normal temperature in the co-presence of iodide ions and iron (III) ions as an oxidant.

Japanese Patent Appln Publication No. H7-91666 (hereafter referred to as Patent Document 2) discloses removing iodine from solution using: active chlorine as an oxidant for oxidizing iodine; activated carbon as adsorbent; and anion exchange resins. In a method for refining alkaline metal chloride solution, a typical method for removing iodine in the solution comprises the following steps: (1) adding chlorine, hypochlorous acid, or chlorine water to solution containing iodine and alkaline metals chlorides; (2) oxidizing iodide ions into iodine molecules ($I_2$); and (3) passing them through activated carbon to adsorb them to the activated carbon. Similarly, Japanese Patent Appln Publication No. H4-16554 (hereafter referred to as Patent Document 3) describes a method for removing iodine from solution using an oxidant and activated carbon in industrial brine electrolysis method. Furthermore, Japanese Patent No. S62-34681 (hereafter referred to as Patent Document 4) describes that ion-exchange resins are used to separate and recover iodine from salt water.

PRIOR ART

Patent Document

[Patent Document 1] Japanese Patent Appln Publication No. 2011-42858
[Patent Document 2] Japanese Patent Appln Publication No. H7-91666
[Patent Document 3] Japanese Patent Appln Publication No. H4-16554
[Patent Document 4] Japanese Patent No. S62-34681

SUMMARY OF THE INVENTION

Problem to be Solved

In the case of Patent Document 1, it would be economically and environmentally desirable to produce and provide iron (III) ions through oxidizing with iron-oxidizing microorganisms from iron (II) ions, which may be obtained as a result of leaching reaction, and/or from ferrous sulfate, which is cheap reagent. It would be also economically and environmentally desirable to recycle post-leaching solution as leaching solution without disposing. However, iodine ingredients (content) are high sterilizability. Therefore, it has been difficult to regenerate iron (III) ions with iron-oxidizing microorganisms in the presence of iodine ingredients (i.e., in solution containing iodine ingredients).

Patent Documents 2-4 disclose a method for separating iodine ingredients. However, the subject solution for removing iodine ingredients is quite different from the acid solution which is used for leaching from a copper sulfide ore and which contains metal ions such as iron and copper. Hence, it is difficult to directly apply the methods disclosed in Patent Documents 2-4 to the one disclosed in Patent Document 1. Furthermore, these methods employ an oxidant containing chlorine, which is toxic for microorganisms. Therefore, even if it is possible to directly apply these method to remove iodine ingredients from leaching solution of a copper sulfide ore, chloride ions or oxidants containing chlorine remain to adversely affect on microorganisms. For these reasons, it has been difficult to use microorganisms to efficiently oxidize iron in solutions where iodine ingredients are removed.

Then, one object of the present invention is, in view of the above descriptions, to provide a method for efficiently regenerating iron (III) ions with the use of microorganisms while leaching copper from a copper sulfide ore in using iodide ion under practical and general conditions.

The present inventors intensively studied to address these problems. As a result, in leaching with iodine ingredients from a copper sulfide ore primarily containing chalcopyrite and enargite, it was found to be effective to react acid solution containing iodide ions and iron (II) ions in a reactor including activated carbon and iron-oxidizing microorganisms. Specifically, reacting in said reactor including them was found to enable to oxidize iron (II) ions in said solution into iron (III) ions with iron-oxidizing microorganisms, and concurrently to adsorb iodine ingredients, which are produced via oxidation by iron (III) ions, into activated carbon to separate and recover said iodine ingredients. The present invention is completed by these observations.

Specifically, the present invention includes the following inventions.

(1). A method for treating acid solution containing iodide ions and iron (II) ions, comprising oxidizing the iron (II) ions in said solution into iron (III) ions by iron-oxidizing microorganisms, wherein the oxidization is carried out in the presence of activated carbon.

(2). The method according to the item (1), wherein the iron (III) ions generated via the oxidation oxidize the iodide ions to generate iodide molecules and/or triiodide ions, and wherein the iodide molecules and/or the triiodide ions is adsorbed to the activated carbon in parallel.

(3). The method according to the item (1) or (2), wherein the acid solution containing the iodide ions and the iron (II) ions is post-leaching solution, and wherein the post-leaching solution is obtained via a process where copper is leached from a copper sulfide ore using sulfuric acid solution as leaching solution containing iodide ions and iron (II) ions.

(4). A method for leaching copper from a copper sulfide ore, comprising using the following solution(s) as leaching solution for a copper sulfide ore:
  solution containing iron (III) ions wherein the acid solution is treated by the method according to the item (2) and is deprived of the activated carbon; and/or
  solution containing iodide ions obtained via the following steps:
    Treating the acid solution by the method according to the item (2);
    Recovering the activated carbon from the acid solution; and
    Reducing into iodide ions the iodide molecules and/or the triiodide ions adsorbed into the activated carbon to release from the activated carbon.

(5). The method for treating or leaching according to any one of the items (1) to (4), wherein the oxidation is carried out in a fluidized bed reactor, and wherein the concentration of the activated carbon in solution is ten times or more relative to that of Iodine at weight ratio.

(6). The method for treating or leaching according to any one of the items (1) to (5), wherein the iron-oxidizing microorganisms are *Acidithiobacillus ferrooxidans*, and the oxidation is carried out under atmospheric pressure.

(7). The method for treating or leaching according to the item (2) or (4), wherein the iodide molecules and/or the triiodide ions adsorbed into the activated carbon is reduced to iodide ions to be released from the activated carbon using solution containing sulfite ions.

Effect of the Invention

According to the present inventions, the following effects may be achieved.

(1) Iron-oxidizing microorganisms produce iron (III) ions from iron (II) ions. The produced iron (III) ions then oxidize iodide ions ($I^-$) to produce iodine molecules ($I_2$) and/or triiodide ions ($I_3^-$). Said iodine molecules and/or triiodide ions is highly toxic to microorganism. However, introducing activated carbon, said iodine molecules ($I_2$) and/or triiodide ions ($I_3^-$) is adsorbed into said activated carbon. In brief, the followings occur concurrently in the same system: (i) oxidizing iron (II) ions by iron-oxidizing microorganisms; (ii) oxidizing iodine ingredients by the produced iron (III) ions; and (iii) adsorbing the iodine ingredients into activated carbon. These oxidations allow for efficient regeneration of iron (III) ions and separating and recovering iodine ingredients.

(2) Said iron (III) ions, which are produced via the mechanism described in the above (1), are mixed with solution containing iodine ingredients. Thereby, reaction system may be constructed where the iodine molecules ($I_2$) and/or the triiodide ions ($I_3^-$), which may be catalysis for reaction of solubilizing a copper sulfide ore, are regenerated to be constantly provided.

Another method except for the present invention may be provided where iodine ingredients in post-leaching solution are recovered by activated carbon and then iron is oxidized by microorganisms. In this case, it is, however, required to add an oxidant such as iron (III) ions into solution to oxidize iodine ingredients for the purpose of adsorbing the iodine ingredients into activated carbon. Furthermore, the activated carbon is required with an amount of 200 times or more at weight ratio relative to the iodine ingredients for moderating toxicity to microorganisms. In contrast, the present invention does not need to add iron (III) ions to post-leaching solution prior to iron-oxidizing treatment. Furthermore, the present invention does not require a large amount of activated carbon such as 200 times or more at weight ratio relative to the iodine ingredients. The present invention thus allows for low-cost and simplified process.

(3) The iodine ingredients being adsorbed into the activated carbon may be eluted with sulfite ions to be recovered. Reuse of the recovered iodine ingredients for leaching solution allows for lower-cost and more-efficient process.

(4) The present invention enables to efficiently leach copper from a copper sulfite ore including chalcopyrite and enargite at normal temperature with low cost.

DETAILED DESCRIPTION OF THE INVENTION

Figure 1:
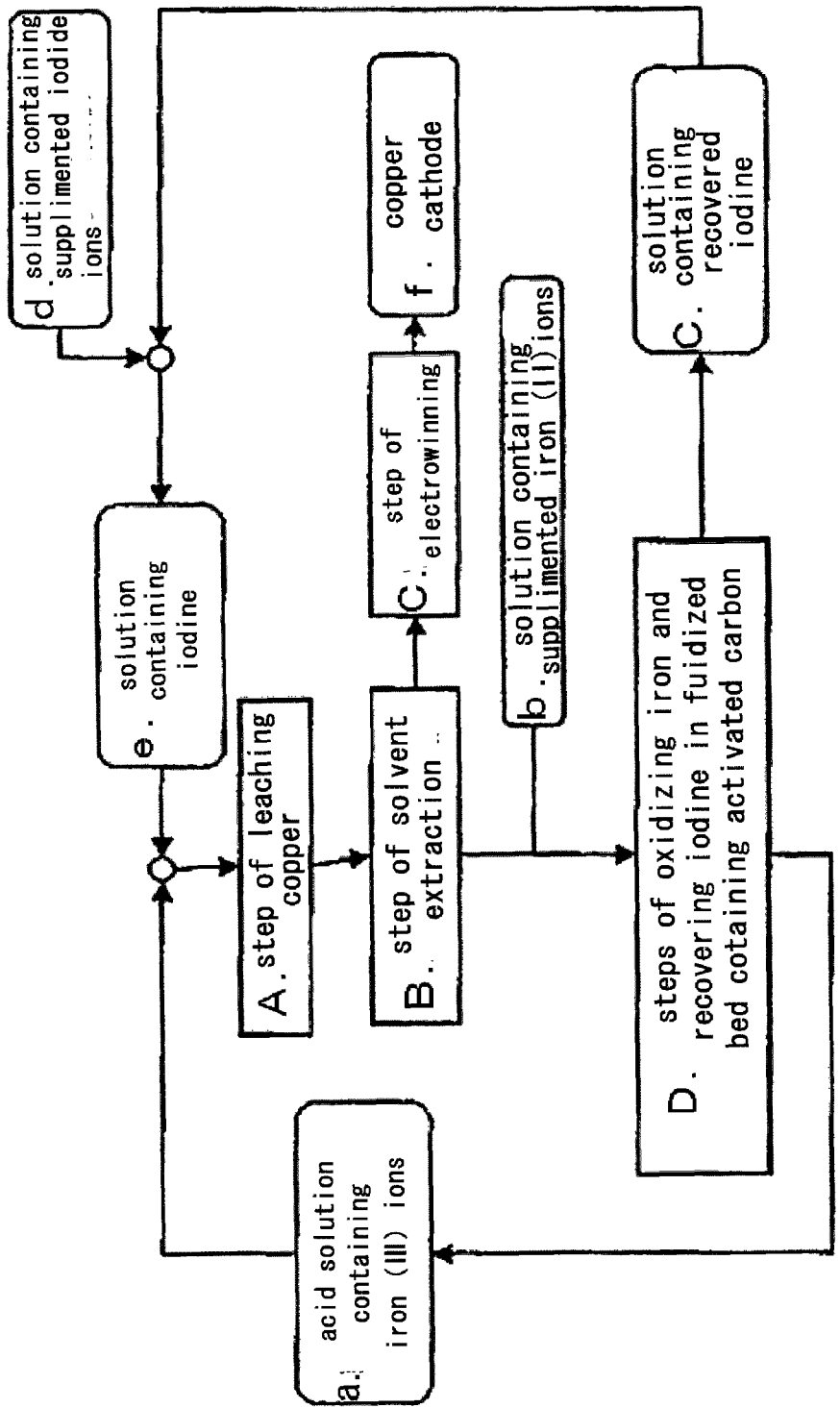
FIG. 1 shows flow diagram for treatment according to the present invention using activated carbon in a fluidized bed reactor.

A method according to the present invention is for treating acid solution containing iodide ions and iron (II) ions. In particular, a method according to the present invention is for producing iron (III) ions from solution containing iodide ions and iron (II) ions. A method according to the present invention further includes a method for separating and recovering iodine ingredients.

In one embodiment according to the present invention, it may be performed in the presence of activated carbon to oxidize iron (II) ions in acid solution (which contains iodide ions and iron (II) ions) into iron (III) ions with iron-oxidizing microorganisms.

In another embodiment according to the present invention, activated carbon and iron-oxidizing microorganisms (such as *Acidithiobacillus ferrooxidans*) may be introduced into solution containing iodide ions and iron (II) ions to react (e.g., aerobically in an iron-oxidizing reactor).

This reaction may produce iron (III) ions, and the resulting iron (III) ions may oxidize iodide ions to produce iodide molecules and/or triiodide ions. Then, the oxidized iodine molecules ($I_2$) and/or triiodide ions ($I_3^-$) may be adsorbed into activated carbon.

Therefore, one advantage of the present invention is to enable to continuously oxidize iron by reducing toxicity of oxidized iodine to iron-oxidizing microorganisms and to separate and recover valuable iodine ingredients.

Furthermore, in one embodiment, the present invention may be applied to a method for leaching copper from a copper sulfide ore using sulfuric acid solution as leaching solution containing iodide ions and iron (III) ions (for example, an excessive amount of iron (III) ions relative to said iodide ions) (FIG. 1A, (a) and (e)). Specifically, activated carbon and iron-oxidizing microorganisms (such as *Acidithiobacillus ferrooxidans*) are introduced, for example aerobically, into solution obtained after the copper-leaching step to be reacted (FIG. 1D). That is, iron (II) ions in the solution, or further supplemented iron (II) ions (FIG. 1b, e.g., ferrous sulfate) are oxidized while iodide ingredients are removed by activated carbon. After that, it may be possible to use the acid solution, which contains iron (III) ions produced with iron-oxidizing microorganisms, for leaching solution of a copper sulfide ore. Alternatively, the acid solution may be mixed with the iodine ingredients, which are recovered after adsorption into activated carbon, to use as leaching solution of a copper sulfide ore.

The copper sulfide ore used in the method according to the present invention contains chalcopyrite or enargite. Moreover, said copper sulfide ore may be the one primarily containing chalcopyrite or enargite. Alternatively, said copper sulfide ore may be the one partially containing chalcopyrite or enargite. Although an amount of chalcopyrite or enargite is not specifically limited, the copper sulfide ore used in the method according to the present invention preferably is the one primarily containing chalcopyrite or enargite in order to achieve sufficient copper-leaching effect by the method according to the present invention.

The method according to the present invention may be applied to any form of leaching as long as said form is hydrometallurgy for leaching copper using sulfuric acid solution as leaching solution. For example, said form of leaching may be not only batch stirred leaching, but also either of heap leaching or dump leaching, in which sulfuric acid is scattered on top of a heap of an ore to leach copper into the sulfuric acid.

Although temperature for leaching is not specifically limited, leaching may be under normal temperature without particular heating.

Without being bound by theory, dissolution and leaching of a copper sulfide ore via the method of the present invention are thought to be preceded according to a series of catalysis reactions which are represented by the following Formulae 1 and 2 which iodine ingredients are involved in.

$$2I^- + 2Fe^{3+} \rightarrow I_2 + 2Fe^{2+} \quad \text{(Formula 1)}$$

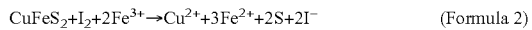

$$CuFeS_2 + I_2 + 2Fe^{3+} \rightarrow Cu^{2+} + 3Fe^{2+} + 2S + 2I^- \quad \text{(Formula 2)}$$

The both side of the above Formulae 1 and 2 are summed to delete the iodine ingredients leading to Formula 3, which is appeared to be conventionally-suggested leaching reaction for a copper sulfide ore using iron (III) ions as an oxidant.

$$CuFeS_2 + 4Fe^{3+} \rightarrow Cu^{2+} + 5Fe^{2+} + 2S \quad \text{(Formula 3)}$$

Initially, in the reaction according to Formula 1, the iodide ions ($I^-$) which is added into leaching solution are oxidized by the iron (III) ions ($Fe^{3+}$) to produce the iodine molecules ($I_2$).

Then the iodine molecules ($I_2$) produced by the reaction of Formula 1 react with the remaining iodide ions ($I^-$), and thereby triiodide ions ($I_3^-$) are also generated in leaching solution.

The concentration of iodine in the leaching solution may be optimized according to a reaction form, or type, shape, or copper grade of a subjective copper sulfide ore (incidentally, the term "the concentration of iodine" used herein refers to total iodine concentration including not only $I_2$, but also any form of iodine such as $I^-$ and $I_3^-$). However, the concentration of iodine is preferably between 100 mg/L and 300 mg as suggested in Japanese Patent Appln Publication No. 2010-24511, or between 8 mg/L and 100 mg/L as suggested in Japanese Patent Appln Publication No. 2011-42858.

As indicated above Formula 3, the iron (III) ions as an oxidant need to be supplied with an amount corresponding to that of a copper sulfide ore ($CuFeS_2$) for leaching the ore. Furthermore, for continuous leaching of a copper sulfide ore, the iron (III) ions as an oxidant need to be continuously supplied. However, iodine ingredients are highly toxic to microorganisms.

Especially in case of utilizing iron-microorganisms, the iodide ions, which is not highly toxic to microorganisms, may be oxidized by the produced iron (III) ions, to be converted into iodine molecules ($I_2$) or triiodide ions ($I_3^-$), which is highly toxic to microorganisms. Thus, even if the concentration of the iodide ions in solution is only 1 ppm, it is found to be difficult to oxidize to produce iron (III) ions using iron-oxidizing microorganisms.

In a typical embodiment of the present invention, activated carbon and iron-oxidizing microorganisms are introduced into post-leaching solution in the same reaction system. Thereby, iron-oxidizing microorganisms may produce iron (III) ion in the same system while iodide ingredients, which are highly toxic to iron-oxidizing microorganisms, are removed from post-leaching solution.

In the present invention, both step of oxidizing iron (II) ions in solution obtained after copper leaching step and step of adsorbing iodine ingredients into activated carbon are preferably performed in parallel in fluidized bed reactor containing the activated carbon and the iron-microorganisms (FIG. 1D). The concentration of activated carbon is also preferably ten times or more at weight ratio relative to the concentration of iodine in the prior-introducing solution, more preferably thirteen times or more. Furthermore, the upper limit of the activated carbon is, but not limited to, for example, 1000 times or less, typically 700 times or less or 150 times or less in view of such as cost.

Moreover, material for removing iodine ingredients is preferably the one being capable of adsorbing the iodine ingredients via hydrophobic interaction.

Hence, other materials except for activated carbon also may be used which have a hydrophobic surface such as cokes or hydrophobic resin. However, activated carbon is particularly preferable because of its large specific surface area and its excellent ability of removing iodine ingredients.

A type and material and other features for activated carbon used for the present invention are not limited to specified ones. However, preferable is activated carbon with large specific surface area, suitability for use in liquid phase, and stability. The shape of activated carbon is preferably granule or sphere. For example, Coconut Shell Mc (Taihei Chemical Industrial Co. Ltd.) and SHIRASAGI X7000H (Japan Enviro Chemicals) may be used.

The concentration of iron (II) ions in solution which is subject of the present invention is not limited to specific concentration. However, it is preferably range from 0.2 g/L to 10 g/L for good growth of iron-oxidizing microorganisms. The aforementioned range of concentration of iron (II) ions is also suitable for post-leaching solution of a copper sulfide ore. The aforementioned range of concentration of iron (II) ions is also suitable for using mixture of solution containing produced iron (III) ions and solution containing iodine ingredients as post-leaching solution of a copper sulfide ore.

The concentration of iodine in solution which is subject of the present invention is not limited to specific concentration. The effect of the present invention is not achieved until the aforementioned concentration is high enough to inhibit the growth of iron-microorganisms in absence of activated carbon. The concentration to inhibit growth is approximately 0.5 mg/L or more.

The adsorbed iodine ingredients also may be recovered to recycle via reagent solution treatment, heating treatment and combustion treatment. In particular, according to the present invention, activated carbon adsorbing iodine ingredients such as iodine molecules and/or triiodide ions may be treated and eluted with solution containing sulfite ions. Thereby, the iodine ingredients adsorbed into the activated carbon may be reduced into iodide ions ($I^-$) to be released (FIG. 1c). Then, the solution containing iodide ions ($I^-$) may be recycled for leaching from a copper sulfide ore. Alternatively, the solution containing iodide ions ($I^-$) may be mixed with acid solution containing iron (III) ion (FIG. 1a) to recycle for leaching from a copper sulfide ore (FIG. 1e). Of course, additional solution containing iodide ions may be supplemented to the recycled solution (FIG. 1d).

In such embodiments, it is preferable to recover the iodide ingredients using solution containing sulfite ions with the amount of 1 to 100 times at weight ratio relative to the iodide ingredients to be eluted. More preferably, the aforementioned amount may be 33 to a 100.

In recovering copper from solution after step of copper leaching (FIG. 1B, C and f), a solvent extraction method may be generally employed which utilizes an extractant for selective extraction of copper. In rare cases, a cementation process may be used.

The above mentioned methods may be performed in any stage (such as before or after step of recovering iodide ingredients or oxidizing iron according to the present invention (FIG. 1D)).

FIG. 1 illustrates an example according to the process flow of the present invention including a solvent extraction step. FIG. 1 depicts an example of a fluidized reactor using activated carbon and iron-oxidizing microorganism. A process is not limited to the serial flow as indicated in FIG. 1. A step of extracting copper or a step of recovering iodine ingredients/oxidizing iron also may be bypassed to be arranged in parallel.

In practical, process flows may be optimized to be applied in view of influence of an extractant on microorganisms.

Iron-oxidizing microorganisms used for the present invention are not limited to specified genus or species. Specifically, the following microorganisms may be used: *Acidithiobacillus ferrooxidans*; *Acidimicrobium ferrooxidans*; the microorganisms belonging to *Leptosprillum* genus; the microorganisms belonging to *Ferroplasma* genus; or the microorganisms belonging to *Acidiplasma*.

Among them, *Acidithiobacillus ferrooxidans* may be preferable for the present invention because it may be used to oxidize iron under ordinary temperature and normal pressure. As one example, *Acidithiobacillus ferrooxidans* FTH6B may be used. Said FTH6B is deposited with the deposition number of NITE BP-780 in National Institute of Technology and Evaluation (NITE) Patent Microorganisms Depositary.

As for temperature and pressure at iron-oxidizing reaction, the conditions may be optimized according to each microorganism.

In case of using *Acidithiobacillus ferrooxidans*, the reaction is preferably proceeded under atmospheric pressure. The temperature is desirably range of from 20° C. to 40° C.

EXAMPLE

The further detailed description for the present invention is provided below via Examples. It should be noted that the present invention is not limited to the following specific examples.

Example 1

Production of iron (III) ions by iron-oxidizing microorganisms in the presence of activated carbon in solution containing iodide ions and iron (II) ions.

(1) 25 mL of the following solution was aliquoted into Erlenmeyer flask (50 mL Volume), of which pH was adjusted to 2.0 using sulfuric acid.

| | |
|---|---|
| $Fe^{2+}$ | 6 g/L |
| $(NH_4)_2SO_4$ | 3 g/L |
| $K_2HPO_4$ | 0.1 g/L |
| $MgSO_4$ | 0.4 g/L |
| $Ca(NO_3)_2$ | 0.01 g/L |

(2) Potassium iodide (KI) and activated carbon (Coconut Shell Mc (Taihei Chemical Industrial Co. Ltd.)) were added to reflect the conditions according the following table 1.
(3) After slightly stirring, iron-oxidizing microorganisms FTH6B was added such that its concentration was $2.5 \times 10^6$ cells/mL.
(4) The solution was moderately shaked at temperature 30° C. under atmospheric pressure to facilitate iron oxidization by iron-oxidizing microorganisms.

The concentrations of iron (II) ions in post microorganism treatment solution under respective conditions were determined by a redox titration method using potassium dichromate. The concentration of the total iron ions including iron (II) ions and iron (III) ions was determined by Inductively Coupled Plasma Atomic Emission Spectroscopy (ICP-AES). The concentration of iron (III) was calculated by the difference between the total concentration of iron ions and the concentration of iron (III) ions.

Figure 2:
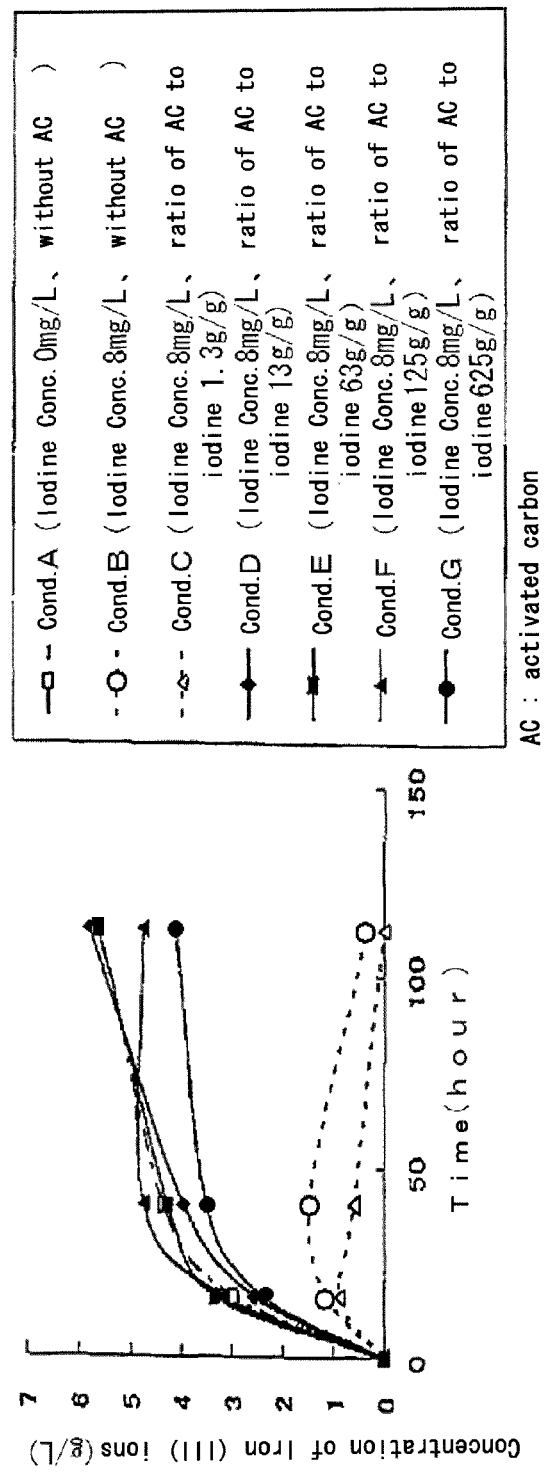
FIG. 2 shows the effect of reducing (moderating) toxicity of iodine on iron-oxidizing microorganisms for each concentration of activated carbon. Iodine is added such that its concentration is 8 mg/L.
Figure 3:
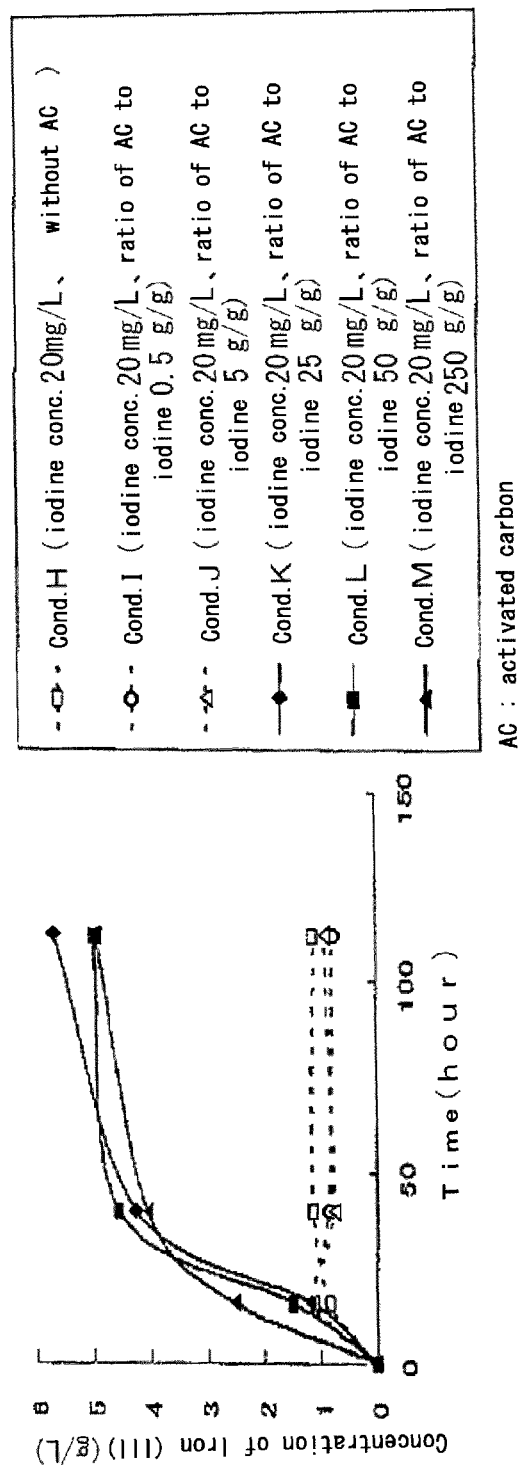
FIG. 3 shows the effect of reducing toxicity of iodine on iron-oxidizing microorganisms for each concentration of activated carbon. Iodine is added such that its concentration is 20 mg/L.

Time course changes for the concentration of iron (III) ions are provided in FIGS. 2 and 3.

The treatment conditions A in the graph of FIG. 2 indicate the iron oxidation by iron oxidizing microorganisms in solution without iodine ingredients. On the other hand, the treatment conditions B indicate the iron oxidation by iron oxidizing microorganisms in solution with 8 mg/L of iodine. Comparing the treatment conditions A with B, the presence of iodine ingredients has been shown to significantly inhibit the iron oxidation by iron oxidizing microorganisms.

In addition, the treatment conditions C to G indicate the iron oxidation by iron oxidizing microorganisms under the conditions where the solution according to the treatment conditions B was further added with 0.01 g/L to 5 g/L of activated carbon. Comparing the treatment conditions A and B with the treatment conditions C to G, the addition of activated carbon has been shown to recover iron oxidation. Such recovery is significant especially in case where the concentration of activated carbon is 13 times or more at weight ratio relative to the concentration of iodine (the treatment conditions D to G).

In FIG. 3, the treatment conditions H indicate the iron oxidation by iron oxidizing microorganisms in solution with 20 mg/L of iodine. In addition, the treatment conditions I to M indicate the iron oxidation by iron oxidizing microorganisms under the conditions where the solution according to the treatment conditions H was further added with 0.01 g/L to 5 g/L of activated carbon. Comparing the treatment conditions H with the treatment conditions I to M, the addition of activated carbon has been shown to recover iron oxidation. Such recovery is significant especially in case where the concentration of activated carbon is 25 times or more at weight ratio relative to the concentration of iodine (the treatment conditions K to M).

Furthermore, the concentration of iodine in post microorganism treatment solution was measured with ICP-Mass Spectrometry (ICP-MS). The result of the measurement is provided in Table 1. The iodine ingredients have been shown to little exist in the solution under the condition of adding activated carbon, being adsorbed into the activated carbon.

TABLE 1

| Treat Cond. | Concentration of iodine in solution before microorganism treatment (mg/L) | Activated carbon (g/L) | Ratio of activated carbon relative to iodine in solution (g/g) | Concentration of iodine in solution after microorganism treatment (mg/L) |
|---|---|---|---|---|
| A | 0 | 0 | 0 | 0 |
| B | 8 | 0 | 0 | 7 |
| C | 8 | 0.01 | 1.3 | Not measured |
| D | 8 | 0.1 | 13 | 0.3 |
| E | 8 | 0.5 | 63 | 0.3 |
| F | 8 | 1 | 125 | Not measured |
| G | 8 | 5 | 625 | Not measured |
| H | 20 | 0 | 0 | 18 |
| I | 20 | 0.01 | 0.5 | Not measured |
| J | 20 | 0.1 | 5 | Not measured |
| K | 20 | 0.5 | 25 | 0.2 |
| L | 20 | 1 | 50 | 0.3 |
| M | 20 | 5 | 250 | Not measured |

The results in FIGS. 2 and 3 show that acid solution containing iodide ions and iron (II) ions is reacted in a reactor including activated carbon and iron-oxidizing microorganisms and thereby, the iron-oxidizing microorganisms are enabled to oxidize the iron (II) ions in said solution into iron (III) ions. Moreover, the results in Table 1 also show that the iron (III) ions oxidize iodine ingredients, enabling it to be adsorbed into activated carbon to be separated and recovered.

Example 2

Recovery of iodine ingredients which are adsorbed into activated carbon in solution containing iodide ions and iron (II) ions in the presence of the activated carbon.
(1) 300 mL solution was introduced into sakaguchi flask (Volume 500 mL), wherein the solution contained 6 g/L of iron (II) ions and its composition was pursuant to Example 1 (1).
(2) Potassium iodide (KI) was added to be 25 mg/L and activated carbon was added to be 1 g/L.
(3) After slightly stirring, iron-oxidizing microorganisms FTH6B was added such that its concentration was $2.5 \times 10^7$ cells/mL.
(4) The solution was moderately shaken at temperature 30° C. under atmospheric pressure to facilitate iron oxidization by iron-oxidizing microorganisms.
(5) After the above microorganisms treatment, the solution is filtered and then precipitation including the activated carbon was recovered.
(6) The recovered precipitation was added with 100 mL of solution containing 24 mM sulfite acid (i.e. 2 g/L, 33 times at weight ratio relative to the iodine ingredients).
(7) The added solution was stirred for 1 hour under normal temperature. Then, the concentration of the eluted iodine ingredients was determined by selective ion electrode method according to the method disclosed in Japanese Patent Application No. 2009-245771. Specifically, all of the iodine ingredients existing as molecular iodine and triiodide ion were reduced to iodide ion by optimally adding zinc powder, and then, the concentration is determined with the iodide selective electrode.
As a result, the concentration of the iodine was 32 mg/L, confirming that the iodine ingredients were eluted. This example shows that the following steps may be performed: (i) acid solution containing iodide ions and iron (II) ions is reacted in a reactor including activated carbon and iron-oxidizing microorganisms; (ii) Thereby, iodine ingredients are adsorbed into the activated carbon; (iii) The activated carbon is recovered and then treated with sulfite acid; (iv) Thereby, the iodine ingredients adsorbed into the activated carbon is eluted into solution to be recovered.

The results in Examples 1 and 2 show that it is possible to prepare aqueous solution containing iron (III) ions and aqueous solution containing iodide ions respectively from solution containing both iron (II) ions and iodide ions. Also shown is that, if each concentration of them is optimized to prepare their mixture and then the mixture is used for leaching from a copper sulfide ore, it may be facilitated to leach copper from a copper sulfide ore.

What is claimed is:

1. A method for treating acid solution containing iodide ions and iron (II) ions, comprising oxidizing the iron (II) ions in said solution into iron (III) ions by iron-oxidizing microorganisms, wherein the oxidizing is carried out in the presence of activated carbon.

2. The method according to claim 1, wherein the iron (III) ions generated via the oxidation oxidize the iodide ions to generate iodide molecules and/or triiodide ions, and wherein the iodide molecules and/or the triiodide ions are adsorbed to the activated carbon.

3. The method according to claim 1, wherein the acid solution containing the iodide ions and the iron (II) ions is post-leaching solution, and wherein the post-leaching solution is obtained via a process where copper is leached from a copper sulfide ore using sulfuric acid solution as leaching solution containing iodide ions and iron (III) ions.

4. A method for leaching copper from a copper sulfide ore, comprising using the following solution(s) as leaching solution for a copper sulfide ore:
solution containing iron (III) ions wherein the acid solution is treated by the method according to claim 2, wherein the activated carbon is removed from said solution; and/or
solution containing iodide ions obtained via the following steps:
treating the acid solution by the method according to claim 2;
recovering the activated carbon from the acid solution; and
reducing into iodide ions the iodide molecules and/or the triiodide ions adsorbed into the activated carbon to release from the activated carbon.

5. The method for treating according to claim 1, wherein the oxidation is carried out in a fluidized bed reactor, and wherein the weight ratio of the activated carbon in solution is ten times or more relative to that of Iodine.

6. The method for treating according to claim 1, wherein the iron-oxidizing microorganisms are *Acidithiobacillus ferrooxidans*, and the oxidation is carried out under atmospheric pressure.

7. The method for treating according to claim 2, wherein the iodide molecules and/or the triiodide ions adsorbed into the activated carbon is reduced to iodide ions to be released from the activated carbon using solution containing sulfite ions.

8. The method according to claim 2, wherein the acid solution containing the iodide ions and the iron (II) ions is post-leaching solution, and wherein the post-leaching solution is obtained via a process where copper is leached from a copper sulfide ore using sulfuric acid solution as leaching solution containing iodide ions and iron (III) ions.

9. The method for treating according to claim 2, wherein the oxidation is carried out in a fluidized bed reactor, and wherein the weight ratio of the activated carbon in solution is ten times or more relative to that of Iodine.

10. The method for treating or leaching according to claim 3, wherein the oxidation is carried out in a fluidized bed reactor, and wherein the weight ratio of the activated carbon in solution is ten times or more relative to that of Iodine.

11. The method for treating or leaching according to claim 4, wherein the oxidation is carried out in a fluidized bed reactor, and wherein the weight ratio of the activated carbon in solution is ten times or more relative to that of Iodine.

12. The method for treating according to claim 2, wherein the iron-oxidizing microorganisms are *Acidithiobacillus ferrooxidans*, and the oxidation is carried out under atmospheric pressure.

13. The method for treating or leaching according to claim 3, wherein the iron-oxidizing microorganisms are *Acidithiobacillus ferrooxidans*, and the oxidation is carried out under atmospheric pressure.

14. The method for treating or leaching according to claim 4, wherein the iron-oxidizing microorganisms are *Acidithiobacillus ferrooxidans*, and the oxidation is carried out under atmospheric pressure.

15. The method for treating according to claim 5, wherein the iron-oxidizing microorganisms are *Acidithiobacillus ferrooxidans*, and the oxidation is carried out under atmospheric pressure.

16. The method for treating or leaching according to claim 4, wherein the iodide molecules and/or the triiodide ions adsorbed into the activated carbon is reduced to iodide ions to be released from the activated carbon using solution containing sulfite ions.

17. The method according to claim 1, wherein the iron (III) ions generated via the oxidation oxidize the iodide ions to generate iodide molecules and/or triiodide ions, and wherein the iodide molecules and/or the triiodide ions are adsorbed to the activated carbon, wherein the iodide molecules and/or triiodide ions are concurrently (a) generated, and (b) adsorbed to the activated carbon.

\* \* \* \* \*